United States Patent [19]
Jones et al.

[11] Patent Number: 5,811,276
[45] Date of Patent: Sep. 22, 1998

[54] METHOD OF PREPARING MICROORGANISMS HAVING THICKENED CELL WALLS USING A MAGNETIC FIELD

[75] Inventors: Craig Jones, Juno Beach; D. Michael Bitz, Miami, both of Fla.

[73] Assignee: E.K.M.A., Inc., Miami, Fla.

[21] Appl. No.: 376,553

[22] Filed: Jan. 20, 1995

[51] Int. Cl.⁶ ............... C12N 1/00; C12N 1/04; C12N 13/00
[52] U.S. Cl. ............ 435/173.4; 424/93.3; 424/93.4; 435/173.1; 435/243; 435/252.1; 435/260; 504/117
[58] Field of Search ............ 435/173.1, 173.4, 435/243, 173.8, 260, 822, 252.1; 504/117; 424/93.3, 93.4

[56] References Cited

U.S. PATENT DOCUMENTS

| | | | |
|---|---|---|---|
| 2,196,361 | 4/1940 | Liebesny et al. | 195/79 |
| 2,767,072 | 10/1956 | Coanda | 71/7 |
| 3,095,359 | 6/1963 | Heller et al. | 195/78 |
| 3,623,265 | 11/1971 | Brunton et al. | 47/1.3 |
| 3,675,367 | 7/1972 | Amburn | 47/1.3 |
| 3,871,961 | 3/1975 | Gianessi | 195/37 |
| 4,487,766 | 12/1984 | Mach | 424/180 |
| 4,508,625 | 4/1985 | Graham | 210/695 |
| 4,828,710 | 5/1989 | Itoh | 210/675 |
| 4,879,045 | 11/1989 | Eggerichs | 210/695 |
| 4,915,915 | 4/1990 | Treharne | 422/186.24 |
| 4,938,875 | 7/1990 | Niessen | 210/695 |

FOREIGN PATENT DOCUMENTS

| | | |
|---|---|---|
| 224 615 | 7/1985 | Germany . |
| 6174629 | 4/1986 | Japan . |
| 3622789 | 3/1987 | Japan . |
| 62-278907 | 3/1987 | Japan . |
| 235987 | 2/1990 | Japan . |
| 0003246 | 12/1971 | U.S.S.R. . |
| WO 93/13725 | 7/1993 | WIPO . |

OTHER PUBLICATIONS

Curtis, Tom "The Old Man and the Secret", Texas Monthly 18(6):112 (1990).

36212969A4, 1987 Japan Patent English Abstract only.

*Primary Examiner*—David M. Naff
*Assistant Examiner*—Deborah K. Ware
*Attorney, Agent, or Firm*—Nixon & Vanderhye P.C.

[57] ABSTRACT

The present invention relates to a composition capable of stimulating plant growth and to a method of preparing such a composition. Also disclosed is a method of preparing a microbial culture containing microorganisms having thickened cell walls. The microorganisms are prepared by passing the microorganisms having cell walls through a magnetic field having two magnets of like north poles which face the microbial culture to be treated. Upon the treatment in the magnetic field the cell walls of the microorganisms become thickened and are effective as an ingredient of a plant growth stimulating composition. Furthermore, a method of stimulating plants such as a vegetable plant, sugar cane, a fruit tree, a tropical plant or a grass is disclosed and is carried out by applying the composition to the plant to effect stimulation of the growth of the plant.

9 Claims, 2 Drawing Sheets

METHOD OF PREPARING MICROORGANISMS HAVING THICKENED CELL WALLS USING A MAGNETIC FIELD

TECHNICAL FIELD

The present invention relates to a composition capable of stimulating plant growth and to a method of preparing such a composition.

BACKGROUND

Plant growth stimulating compositions have application in a number of areas, including farming and commercial and residential landscape maintenance. Various growth stimulating compositions are available that are derived from natural or from synthetic sources. The compositions of the present invention have constituents from both sources and have the advantage of superior growth stimulatory properties. The compositions of the present invention have the further advantage that they can be tailored so as to be optimum for a particular plant type growing under particular soil conditions.

OBJECTS AND SUMMARY OF THE INVENTION

It is an object of the present invention to provide a composition capable of stimulating the growth of plants.

It is another object of the invention to provide a method of treating a microbial culture so as to render it suitable for use as a constituent of a plant growth stimulating composition.

It is a further object of the invention to provide a nutrient formulation suitable for use as a constituent of a plant growth stimulating composition.

In one embodiment, the present invention relates to a method of preparing a culture of microorganisms for use as a constituent of a plant growth stimulating composition. The method comprises:
  i) obtaining a starting culture sample of microorganisms from the gastrointestinal track of a mammal;
  ii) culturing the sample in a medium comprising sodium, potassium, calcium, magnesium, inorganic phosphorus and chlorine or salts thereof;
  iii) culturing the sample resulting from step (ii) in the presence of a food source comprising a grain or a grass;
  iv) separating the culture of microorganisms resulting from step (iii) from the food source; and
  v) exposing the culture resulting from step (iv) to a magnetic field.

In a further embodiment, the present invention relates to a plant growth stimulating composition comprising a culture of microorganisms produced by the above method and a nutrient formulation comprising Na, Cl, P, Mg, Ca, S, Zn, Cu, Co, I, Se, Fe, K, Mn, Mo, Si, B, Ni and Rb. In yet a further embodiment, the present invention relates to such a nutrient formulation.

In still another embodiment, the present invention relates to method of stimulating the growth of a plant. The method comprises administering to the plant the above composition under conditions such that the stimulation is effected.

In yet another embodiment, the present invention relates to a method of preparing a culture of microorganisms for use as a constituent of a plant growth stimulating composition comprising exposing the culture to a magnetic field under conditions such that thickening of the cell walls of the microorganisms, as determined by light microscopy, is effected.

Further objects and advantages of the present invention will be clear from the description that follows.

DETAILED DESCRIPTION OF THE INVENTION

Figure 1:
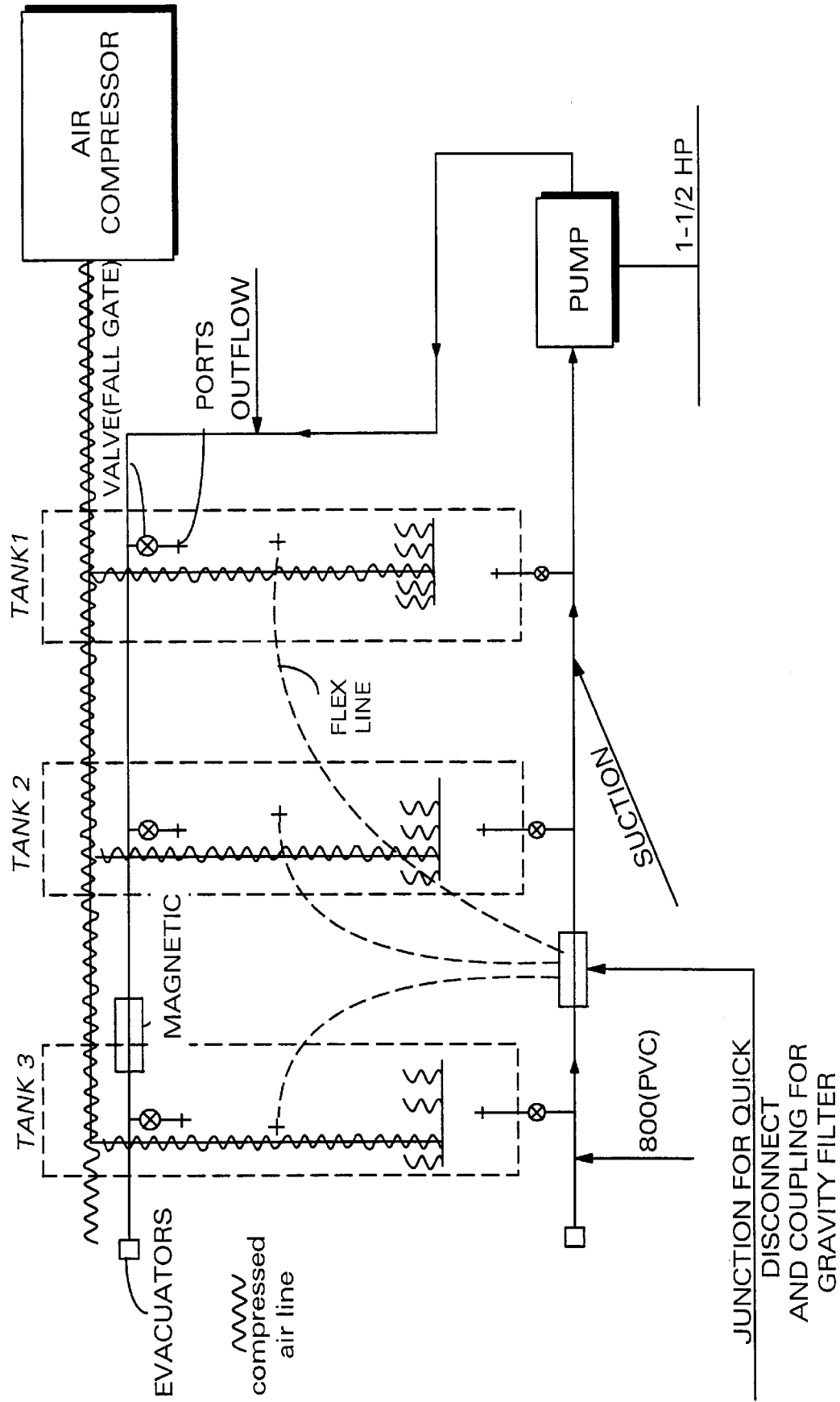
FIG. 1. Diagram of fermentation tanks for preparation of microbial cultures.

The present invention relates to a method of preparing microbial cultures for use as constituents of a plant growth stimulating compositions. The invention also relates to nutrient formulations to be used in combination with such microbial cultures in the growth stimulating compositions. The cultures and formulations of the invention can be used to stimulate the growth of a variety of plant types including sugar cane, vegetables, fruits, grasses and tropical plants. The cultures and formulations can also be used to advantage on ornamental plants.

Starting cultures suitable for use in preparing the microbial cultures of the invention can be obtained by combining isolates of specific microbial strains or by obtaining a mixed culture from an animal, for example, from the gastrointestinal track of an animal, preferably, a mammal, more preferably a herbivore, most preferably a cow (eg a lactating cow). Starting cultures can be obtained, for example, from a sample aspirated from the stomach of an animal (eg from the rumen of a herbivore) or from a fecal sample taken from the intestinal track of an animal.

The starting culture, whether obtained from a natural source or prepared from isolates, is cultured for an initial period (eg 21 to 31 hours, preferably, 24 hours) in the presence of a medium that can be prepared from natural sources (eg from the saliva of a herbivore (eg a cow)) or from chemicals. When prepared from saliva, the following procedure can be used. A bolus (eg about 1 liter) is taken from the mouth of the animal (eg a cow) and placed on a filter (eg about an 80 micron filter). The bolus is washed with warm water (about 10 liters of water per liter of bolus) and the filtrate (pH preferably about 6.3 to 6.8) is obtained and used as the initial culture medium.

When synthetic medium is used, it is preferably formulated so as to contain the following:
  sodium
  potassium
  calcium
  magnesium
  inorganic phosphorus
  chloride As an example, a culture medium containing the following can be used:

| | |
|---|---|
| Sodium bicarbonate | .0225 g/liter |
| Potassium bicarbonate | .00125 g/liter |
| Calcium carbonate | .000025 g/liter |
| Magnesium carbonate (anhydrous) | .0000375 g/liter |
| Phosphoric acid | .003375 g/liter |
| Chloroacetic acid | .002125 g/liter |

The concentrations of the culture medium components can vary depending on the starting culture and on the target plant, however, typically concentrations vary, for example, by plus or minus 45%, preferably, plus or minus 20% from the above.

The starting culture sample is incubated in the culture medium, preferably, at a pH in the range of 6.9 to 7.3. Adjustments in pH can be made at this point and throughout the process using a variety of acids and bases, sulfuric, hydrochloric and citric being the preferred acids, citric being more preferred, and potassium hydroxide, calcium hydroxide and sodium bicarbonate being the preferred bases, sodium bicarbonate being most preferred. During this initial incubation period, and throughout the process, air is introduced (eg by compressed air injection) to maintain an oxygen content in the range of 3 to 5 ppm. During this initial period, nitrogen, sugar and oxygen uptake occurs. Cells increase in number, nutrient content and in cell-wall content.

A food source (substrate) is subsequently (eg after about 23 to 28 hrs, preferably 24 hrs) added to the medium/starting culture sample mixture. The food source can comprise a mixture of feed grains and grasses. Preferably, at least three of the following are added in approximately equal parts by weight:

crushed corn oats milo alfalfa sunflower seeds peanuts (whole)

wheat soybeans barley rice flax.

For sugar cane and vegetable crops, a mixture of crushed corn, oats, alfalfa and whole peanuts is preferred. The same is advantageous for tropical plants. When grasses are the target plant (eg in the case of golf course maintenance), a mixture of crushed corn, oats, alfalfa and flax is preferred. The food source is typically added to the medium/starting culture sample together with a further volume of liquid (ie culture medium and water (eg in a ratio of about 1:5 to 1:4)) in a ratio of about 1 kg of dry matter to about 7–8 liters of liquid. Multiple additions of food source and liquid to the original medium/starting culture sample can be made, 2 additions at approximately 24 hour intervals being preferred.

Throughout this period of incubation, an approximately neutral pH is maintained, a pH in the range of about 6.9 to about 7.3 being preferred. The temperature is maintained, preferably, in the range of about 34° to 41° C., 37° to 40° C. being preferred.

After the final addition of food substrate, the resulting broth is well mixed, for example, by recirculating the broth in a recirulation tank. The recirculation is typically for a period of about 24 hours, after which time the broth is allowed to stand for a period sufficient to allow the particulate matter to settle out.

An aliquot of the broth supernatant is then removed and placed in a second container (tank). By separating the supernatant aliquot from the particulate matter, the microorganisms present in the aliquot are separated from their food source (thereby causing a "secondary shunt metabolism" to be effected). The pH of the transferred aliquot is slowly reduced (eg over a period of several hours) to about 4.5 to about 6.3, 5.8 to 6.3 being preferred. The temperature is maintained in the range of about 34° C. to 41°, 37° to 41° C. being preferred. A minimal amount of a second food source is added (eg about 1%–3% v/v of the aliquot, 3% being preferred). The second food source is, for example, molasses (eg sugar cane or citrus molasses), aloe vera, papaya juice, stearate or glycogen. Sugar cane molasses is preferred when sugar cane or grass is the target plant, citric molasses being preferred in the case of citrus and vegetable crops as well as tropical plants (papaya juice can also be advantageous in the case of tropical plants).

At this point in the process, the number of cells per ml is, advantageously, in the range of 700,000 to 1.5 million, about 850,000 cells/ml to 900,000 cells/ml being preferred, around 890,000 cells/ml being most preferred. The cell count can be increased by delaying the transfer of the aliquot from the first tank to the second.

Figure 2:
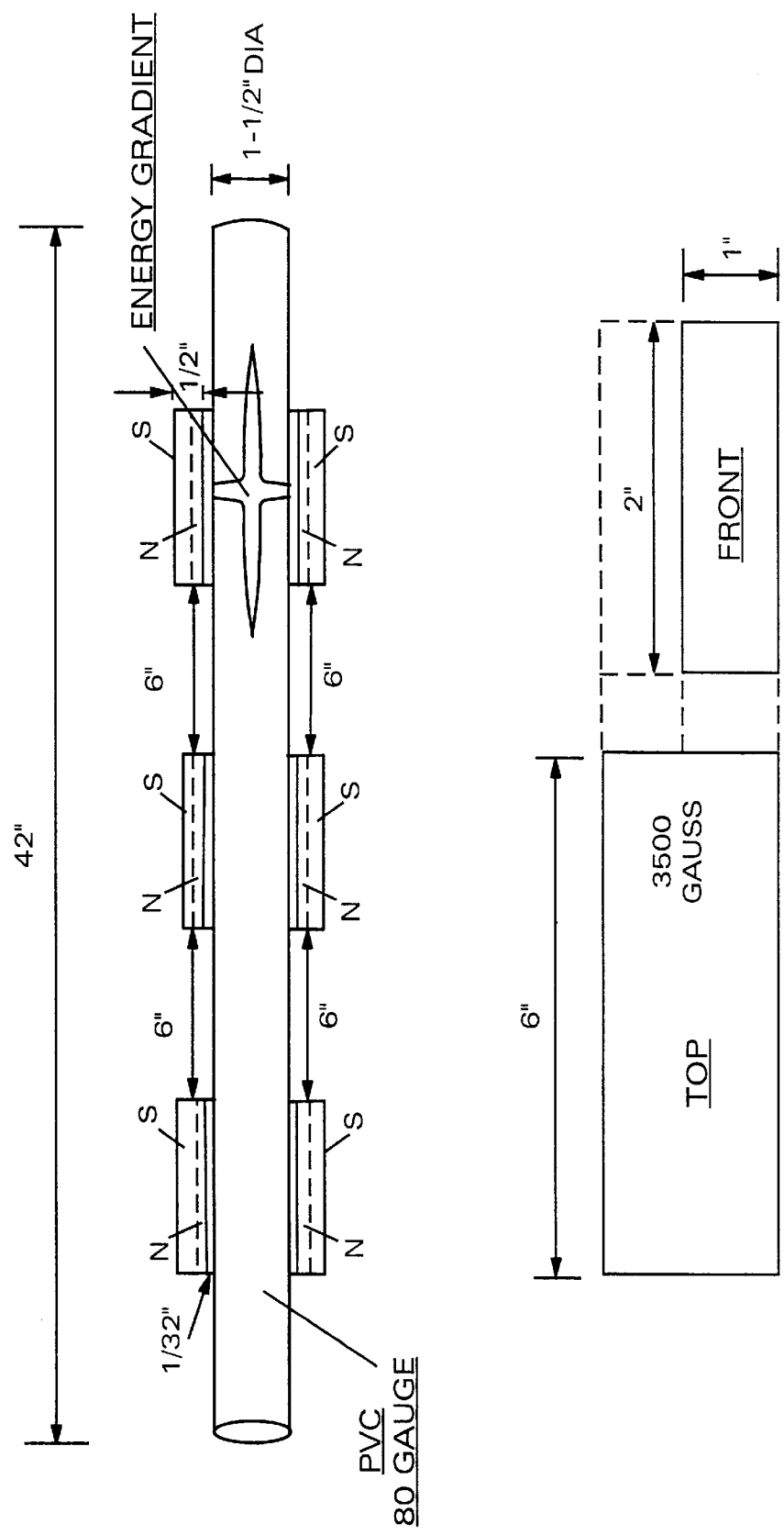
FIG. 2. Diagram of orientation of magnets relative to recirculation tube.

After the pH has been reduced and the second food source added, an aliquot of the culture is recirculated through a magnetic field. The field is created using an electromagnet or permanent magnets, for example, rare earth magnets. In the case of permanent magnets, an appropriate field can be created, for example, by two opposing magnets. Magnets suitable for use in the present invention have a strength in the range of 1200 to 4500 gauss, about 3500 gauss magnets being preferred. FIG. 2 includes a diagram of a preferred orientation of such magnets. While, in the Figure, like poles (ie north poles) are shown to face either side of the recirculation tube, such need not be the case (e.g. opposite poles can also face the tube).

The exposure of the microorganisms to the magnetic field results in an increase in the thickness of the microbial cell wall and an increase in cell mobility, as viewed under light microscopy. The invention contemplates the use of magnetic fields that can achieve these ends.

During the process of recirculation through the magnetic field, a formulation of nutrients is added that includes Na, Cl, P, Mg, Ca, S, Zn, Cu, Fe, K, Mn, Mo, Si, B, Ni, and Rb, preferably, also Co, I, or Se. Preferably, the formulation has the following composition and the concentration ranges listed (g/l) reflect the increase in concentration of the components in the culture upon addition of the formulation to the culture:

|  | Broad range (g/l) | Preferred Range (g/l) |
|---|---|---|
| Sodium bicarbonate | .0001–.10 | .0005–.090 |
| Chloroacetic acid | .0001–.04 | .0005–.03 |
| Phosphoric acid (liquid) | .001–.05 | .002–.02 |
| Magnesium carbonate (anhydrous) | .000075–.05 | .001–.004 |
| Calcium carbonate | .000250–.300 | .001–.004 |
| Sulfur (from sulfates in composition) | .000075–.04 | .002–.006 |
| Zinc stearate | .00004–.008 | .0003–.005 |
| Copper sulfate | .00000001–.06 | .00000001–.00001 |
| Cobalt acetate tetrahydrate | .0000005–.0000000006 | .00000004–.000000003 |
| Iodine (liquid) | .000000003–.000006 | .00000005–.000000008 |
| Se (plasma grade std (liquid)) | .000000003–.00001 | .00000002–.000001 |

-continued

|  | Broad range (g/l) | Preferred Range (g/l) |
|---|---|---|
| Iron sulfate | .0000002–.00009 | .000005–.00006 |
| Potassium bicarbonate | .05–.0006 | .04–.006 |
| Manganese sulfate monohydrate | .000005–.0045 | .00045–.00003 |
| Molybdic acid 85% (powder) | .00000001–.00004 | .00000019–.000005 |
| Silicon (reference std solution (1000 ppm)) | .0000005–.0005 | .00005–.0001 |
| Boric acid | .000002–.0000000003 | .00000003–.0000002 |
| Nickle carbonate | .000000005–.00005 | .0000005–.000003 |
| Rubidium chloride | .000000009–.0000095 | .00000006–.00000055 |

Other forms of the indicated elements can also be used so long as they are acceptable to the microorganisms.

Formulations advantageous for tropical plants, vegetables and grass (eg golf course grass) are as follows (expressed in g/l of culture, the form in which each is added being as indicated above) (see Example for sugar cane values):

|  | Tropical Plants | Vegetables | Golf Course Grass |
|---|---|---|---|
| Na | .018 | .018 | .018 |
| Cl | .003 | .003 | .003 |
| P | .002 | .002 | .002 |
| Mg | .004 | .0031 | .0035 |
| Ca | .004 | .004 | .004 |
| S | .006 | .006 | .006 |
| Zn | .00003 | .00003 | .000038 |
| Cu | .00002 | .00002 | .00002 |
| Co | .00000008 | .00000005 | .000000009 |
| I | .0000008 | .0000008 | .0000008 |
| Se | .0000006 | .00000045 | .00000064 |
| Fe | .00006 | .00006 | .00006 |
| K | .006 | .006 | .006 |
| Mn | .00001 | .00001 | .00001 |
| Mo | .000003 | .000004 | .000009 |
| Si | .00001 | .00001 | .00001 |
| B | .000005 | .000005 | .000005 |
| Ni | .0000003 | .0000003 | .0000003 |
| Rb | .000007 | .000007 | .000007 |

These advantageous values (and those for sugar cane) can vary. The values for tropical plants can vary, for example, by plus or minus 59%, preferably, plus or minus 28%; the values for vegetables by plus or minus 430%, preferably, plus or minus 22%; the values for grass by plus or minus 450%, preferably, plus or minus 20%; and the values for sugar cane by plus or minus 45%, preferably, 20%.

Upon completion of the magnetic field exposure and nutrient formulation addition, the resulting composition can be used immediately or stored, for example, for as long as two years. During storage, the pH is maintained, preferably, between 5.5 and 6.5 and the temperature between 5° C. and 45° C., a temperature in the range of 34°–41° C. being preferred. Storage in the absence of ultra violet light is preferred.

The regimen used to apply the composition can be optimized for any particular plant. By way of example, 1.5 gallons of the composition can be applied per acre to a sugar cane crop per year in approximately four equal applications; about two gallons can be applied per acre of citrus grove per year in two equal applications; about 3 gallons can be applied per acre of golf course grass in two equal applications; and for vegetable crops, about 2–2.5 gallons can be applied per acre per year in two equal applications. In the case of tropical plants, about 1 gallon can be applied per acre per month. The composition is, advantageously, diluted about 20:1 with water and applied by the spraying of the diluted composition, however, other modes of application (eg irragation) can also be used. Foliar spraying is preferred in the case of tropical plants. Application of the composition results in a significant stimulation of plant growth. The composition can be applied alone or with other agents, such as insecticides and herbicides.

Certain aspects of the invention are described in greater detail in the non-limiting Example that follows.

EXAMPLE

Preparation of Composition for Stimulating Growth of Sugar Cane

Approximately a one liter sample is aspirated from the rumen of a 7.5 year old lactating Holstein cow using a rumen aspirator (Johnson and Johnson). The sample is taken about 12–14 hours after feeding. Observed microscopically, the sample includes Clostridia, Baccilus, Azotabacter and protozoa (at least 100 cells of each per ml of sample). The one liter sample is added to a culture medium (169 liters) that includes:

| Culture medium: | |
|---|---|
| Sodium bicarbonate | 3.80 g |
| Potassium bicarbonate | 0.21125 g |
| Calcium carbonate | 0.004225 g |
| Magnesium carbonate (anhydrous) | 0.0063375 g |
| Phosphoric acid | 0.570375 g |
| Chloroacetic acid | 0.359125 g |

The sample and the culture medium (Mixture A) are maintained in Tank 1 (see FIG. 1) at a temperature of 37° C. and at a pH in the range of 6.9–7.3 for a first 24 hour period. At this stage, and throughout the process, pH adjustments are made using citric acid or sodium bicarbonate, as appropriate. During this first 24 hr period, Mixture (A) is agitated by the injection of compressed air which results in the presence in Mixture (A) of about 3–5 ppm oxygen.

At the end of the first 24 hour period, Mixture (B) is added to Mixture (A) in Tank 1. Mixture (B) comprises 140 liters of water, pH 7.0–7.1, and 30 liters of the culture medium described above into which air has been injected to achieve an oxygen content of 3–5 ppm. Mixture (B) also includes approximately 20 kg of a substrate comprising the following in approximately equal parts by weight:

Substrate:

crushed corn oats alfalfa whole peanuts

The pH of Mixture (B) is maintained at about 7.1 to 7.2, the temperature at about 34°–40° C., and the oxygen content at about 3–5 ppm (by injection of compressed air). These same conditions are maintained after the addition of Mixture (B) to Mixture (A) to form Mixture (C). Mixture (C) is maintained in Tank 1 at about 37° C. for a second 24 hr period with agitation by compressed air injection.

At the end of this second 24 hour period, Mixture (D) is added to Mixture (C) in Tank 1 to yield Mixture (E). Mixture (D), like Mixture (B), comprises 140 liters of water, pH 7.1 to 7.2, and 30 liters of culture medium. Mixture (D) also includes 20 kg of the substrate described above. Mixture (E) is maintained in Tank 1 for a third 24 hr period with agitation by compressed air injection (temperature 40° C.; pH 7.1; oxygen content 3–5 ppm).

At the completion of the third 24 hour period, Mixture (E) is recirculated for ten minute periods. Tank 1, and the recirculation system associated therewith, is designed such that complete recirculation of Mixture (E) can be effected in the ten minute period. That recirculation is carried out at two hour intervals for a fourth 24 hour period. Mixture (E) is then allowed to stand for a time sufficient to permit particulate matter to settle out.

At the end of that fourth 24 hour period, 170 liters of Mixture (E) supernatant is transferred to Tank 2 (see FIG. 1). Compressed air is injected into Tank 2 to effect agitation of the aliquot of Mixture (E) present therein (Mixture (E-T2)) and to maintain an oxygen content of 3–5 ppm. Mixture (E-T2) is maintained at a temperature of 37°–41° C. and the pH is slowly reduced to 5.8–6.3 (ie over about a 3 hour period) and 3% (v/v) sugar cane molasses is added. The number of microorganisms present in Mixture (E-T2) is about 890,000 cells per ml.

Mixture (E-T2) (175 liters) is transferred to a further recirculation tank, Tank 3 (see FIG. 1) and a "micronutrient" package is added. The contents of the package is formulated so that the addition thereof to the 175 liters results in the following concentrations, expressed as g/l of Mixture (E-T2):

| | |
|---|---|
| Sodium bicarbonate | .018 |
| Chloroacetic acid | .003 |
| Phosphoric acid (liquid) | .002 |
| Magnesium carbonate (anhydrous) | .002 |
| Calcium carbonate | .004 |
| Sulfur (from sulfates in composition) | .006 |
| Zinc stearate | .00003 |
| Copper sulfate | .00002 |
| Cobalt acetate tetrahydrate | .00000004 |
| Iodine (liquid) | .0000008 |
| Se (plasma grade std (liquid)) | .000001 |
| Iron sulfate | .00006 |
| Potassium bicarbonate | .006 |
| Manganese sulfate monohydrate | .00001 |
| Molybdic acid 85% (powder) | .000001 |
| Silicon (reference std solution (1000 ppm) | .00001 |
| Boric acid | .000005 |
| Nickle carbonate | .00000005 |
| Rubidium chloride | .000007 |

The content of Tank 3 (Mixture (E-T3)) is recirculated, and, during recirculation, is passed though a magnetic field (an 80 gal/min pump is used in the recirculation process). The field is generated by six 3500 gauss rare earth magnets oriented as shown in FIG. 2 with respect to a 1½" diameter PVP 80 gauge recirculation tube, a ⅟₃₂" phenolic band being located between the magnets and the tube. During recirculation, the pH is maintained at between 5.5 and 6.5 and the temperature at about 37° C. Compressed air is injected during recirculation to maintain an oxygen content of 3–5 ppm. The composition resulting after 10 minutes of recirculation is stored for about 24 hours at a temperature of 35°–38° C.

The composition resulting from the foregoing process is applied to sugar cane by spraying four times per year for a total annual application of 1.5 gallons per acre.

\* \* \*

All documents cited above are hereby incorporated in their entirety by reference.

One skilled in the art will appreciate from a reading of this disclosure that various changes in form and detail can be made without departing from the true scope of the invention.

What is claimed is:

1. A method of preparing a microbial culture comprising microorganisms having thickened cell walls, said method comprising:
   i) obtaining a starting microbial culture sample from the gastrointestinal track of a mammal, wherein said starting microbial culture comprises microorganisms having cell walls;
   ii) culturing said starting microbial culture in a culture medium comprising sodium, potassium, calcium, magnesium, inorganic phosphorus and chlorine or salts thereof;
   iii) culturing the microbial culture resulting from step (ii) in the presence of a food source comprising a grain or a grass;
   iv) separating the microbial culture resulting from step (iii) from said food source;
   v) passing said microbial culture resulting from step (iv) through a magnetic field under conditions wherein the cell walls of said microorganisms are thickened as determined by light microscopy.

2. The method according to claim 1 wherein said starting microbial culture is obtained from a herbivore.

3. The method according to claim 2 wherein said starting microbial culture is obtained from the rumen of a cow.

4. The method according to claim 1 wherein said food source comprises at least one of corn, oats, milo, alfalfa, sunflower seeds, peanuts, wheat, soy beans, barley, rice or flax.

5. The method according to claim 1 wherein a pH of 6.9 to 7.3 is maintained in steps (i) to (iii).

6. The method according to claim 5 wherein, in step (iv), the pH is adjusted to 5.8 to 6.3.

7. The method according to claim 1 wherein said magnetic field is generated by at least two rare earth magnets having a range between 1200 to 4500 gauss.

8. The method according to claim 1 wherein the magnetic field of step (v), is generated by two magnets wherein like poles of said magnets face said microbial culture resulting from step (iv).

9. The method according to claim 8 wherein said like poles are north poles.

\* \* \* \* \*

UNITED STATES PATENT AND TRADEMARK OFFICE
CERTIFICATE OF CORRECTION

PATENT NO. : 5,811,276

DATED : September 22, 1998

INVENTOR(S) : Jones, et al.

It is certified that error appears in the above-identified patent and that said Letters Patent is hereby corrected as shown below:

Column 2, line 6, after "cultures." Insert—The line through the junction is 1 ½" diameter, the flex line is 1 ½ " and the ports are 1 ½".

Signed and Sealed this

Sixteenth Day of March, 1999

*Attest:*

Q. TODD DICKINSON

*Attesting Officer*      *Acting Commissioner of Patents and Trademarks*

UNITED STATES PATENT AND TRADEMARK OFFICE
CERTIFICATE OF CORRECTION

PATENT NO.   : 5,811,276

DATED        : September 22, 1998

INVENTOR(S)  : Craig Jones, et al.

It is certified that error appears in the above-identified patent and that said Letters Patent is hereby corrected as shown below:

Column 8, line 21, after "culture" delete "sample".

Signed and Sealed this

Twenty-first Day of December, 1999

*Attest:*

Q. TODD DICKINSON

*Attesting Officer*   *Acting Commissioner of Patents and Trademarks*